(12) United States Patent
Yan

(10) Patent No.: US 8,007,529 B2
(45) Date of Patent: Aug. 30, 2011

(54) MEDICATED POROUS METAL PROSTHESIS

(75) Inventor: John Y. Yan, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/184,347

(22) Filed: Aug. 1, 2008

(65) Prior Publication Data
US 2008/0288058 A1   Nov. 20, 2008

Related U.S. Application Data

(60) Division of application No. 10/767,296, filed on Jan. 28, 2004, now Pat. No. 7,699,890, which is a division of application No. 10/235,033, filed on Sep. 3, 2002, now Pat. No. 6,723,120, which is a continuation of application No. 09/797,313, filed on Mar. 1, 2001, now abandoned, which is a division of application No. 08/837,993, filed on Apr. 15, 1997, now Pat. No. 6,240,616.

(51) Int. Cl.
*A61F 2/06* (2006.01)
(52) U.S. Cl. ....... 623/1.39; 623/1.4; 623/1.42; 623/1.44
(58) Field of Classification Search ................. 623/1.15, 623/1.4, 1.42, 1.44, 1.5, 1.51, 1.53, 1.39
See application file for complete search history.

(56) References Cited

U.S. PATENT DOCUMENTS

| | | | |
|---|---|---|---|
| 3,687,135 A | 8/1972 | Stroganov et al. | |
| 3,839,743 A | 10/1974 | Schwarcz | |
| 3,855,638 A | 12/1974 | Pilliar | 3/1 |
| 3,900,632 A | 8/1975 | Robinson | |
| 4,073,999 A | 2/1978 | Bryan et al. | |
| 4,101,984 A | 7/1978 | MacGregor | 3/1.5 |
| 4,104,410 A | 8/1978 | Malecki | |
| 4,110,497 A | 8/1978 | Hoel | |
| 4,321,711 A | 3/1982 | Mano | 3/1.4 |
| 4,346,028 A | 8/1982 | Griffith | |
| 4,355,426 A | 10/1982 | MacGregor | 3/1.4 |
| 4,374,669 A | 2/1983 | MacGregor | 75/208 R |
| 4,405,319 A | 9/1983 | Cosentino | |
| 4,458,366 A | 7/1984 | MacGregor | |

(Continued)

FOREIGN PATENT DOCUMENTS
DE    44 07 079    9/1994
(Continued)

OTHER PUBLICATIONS
U.S. Appl. No. 10/317,435, filed Dec. 11, 2002, Hossainy et al.
(Continued)

*Primary Examiner* — David Isabella
*Assistant Examiner* — Seema Swaminathan
(74) *Attorney, Agent, or Firm* — Squire, Sanders & Dempsey (US) LLP

(57) ABSTRACT

A porous prosthesis for delivering a medication to the site of implantation. The prosthesis, such as a stent, includes a first porous region and a second porous region and is at least partially formed from a molybdenum-rhenium alloy. The porous regions can have different porosity. A stent includes first, second and third porous region, the first porous region being between the second and third porous regions, and a therapeutic agent is disposed in the first porous region. A stent can also include a solid core and inner and outer porous layers surrounding the core.

11 Claims, 5 Drawing Sheets

U.S. PATENT DOCUMENTS

| | | |
|---|---|---|
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,693,721 A | 9/1987 | Ducheyne ............... 623/16 |
| 4,718,907 A | 1/1988 | Karwoski et al. |
| 4,722,335 A | 2/1988 | Vilasi |
| 4,723,549 A | 2/1988 | Wholey et al. |
| 4,729,871 A | 3/1988 | Morimoto ............... 419/2 |
| 4,732,152 A | 3/1988 | Wallstén et al. |
| 4,733,665 A | 3/1988 | Palmaz ............... 128/343 |
| 4,739,762 A | 4/1988 | Palmaz |
| 4,740,207 A | 4/1988 | Kreamer |
| 4,743,252 A | 5/1988 | Martin, Jr. et al. |
| 4,760,849 A | 8/1988 | Kropf |
| 4,768,507 A | 9/1988 | Fischell et al. |
| 4,776,337 A | 10/1988 | Palmaz |
| 4,776,337 A | 10/1988 | Palmaz |
| 4,800,882 A | 1/1989 | Gianturco ............... 128/343 |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor ............... 128/343 |
| 4,902,289 A | 2/1990 | Yannas |
| 4,977,901 A | 12/1990 | Ofstead |
| 4,994,298 A | 2/1991 | Yasuda |
| 5,015,253 A | 5/1991 | MacGregor |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A * | 11/1992 | Pinchuk ............... 623/23.49 |
| 5,167,614 A | 12/1992 | Tessmann et al. |
| 5,171,262 A | 12/1992 | MacGregor |
| 5,192,311 A | 3/1993 | King et al. |
| 5,197,977 A | 3/1993 | Hoffman, Jr. et al. |
| 5,234,456 A | 8/1993 | Silvestini ............... 606/194 |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,370,682 A | 12/1994 | Schmitt ............... 623/1 |
| 5,370,684 A | 12/1994 | Vallana et al. ............... 623/1 |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,419,760 A | 5/1995 | Narciso, Jr. ............... 604/8 |
| 5,423,885 A | 6/1995 | Williams |
| 5,433,909 A | 7/1995 | Martakos et al. ............... 264/209.1 |
| 5,437,834 A | 8/1995 | Okimatsu et al. ............... 419/24 |
| 5,441,515 A | 8/1995 | Khosravi et al. ............... 606/194 |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. ............... 427/2.3 |
| 5,477,864 A | 12/1995 | Davidson |
| 5,492,768 A | 2/1996 | Okimatsu et al. ............... 427/549 |
| 5,502,158 A | 3/1996 | Sinclair et al. |
| 5,514,379 A | 5/1996 | Weissleder et al. |
| 5,522,894 A | 6/1996 | Draenert ............... 623/16 |
| 5,527,337 A | 6/1996 | Stack et al. ............... 606/198 |
| 5,540,712 A | 7/1996 | Kleshinski et al. |
| 5,545,408 A | 8/1996 | Trigg et al. |
| 5,554,120 A | 9/1996 | Chen et al. |
| 5,556,413 A | 9/1996 | Lam |
| 5,571,187 A | 11/1996 | Devanathan ............... 623/16 |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,693 A | 2/1997 | Seare, Jr. ............... 424/400 |
| 5,605,696 A | 2/1997 | Eury et al. ............... 424/423 |
| 5,607,442 A | 3/1997 | Fischell et al. |
| 5,607,463 A | 3/1997 | Schwartz et al. ............... 623/1 |
| 5,607,467 A | 3/1997 | Froix |
| 5,618,299 A | 4/1997 | Khosravi et al. |
| 5,624,411 A | 4/1997 | Tuch ............... 604/265 |
| 5,629,077 A | 5/1997 | Turnlund et al. |
| 5,630,840 A | 5/1997 | Mayer ............... 623/1 |
| 5,631,135 A | 5/1997 | Gryaznov et al. |
| 5,632,771 A | 5/1997 | Boatman et al. |
| 5,632,779 A | 5/1997 | Davidson ............... 623/12 |
| 5,632,840 A | 5/1997 | Campbell |
| 5,637,113 A | 6/1997 | Tartaglia et al. |
| 5,641,443 A * | 6/1997 | Calcote et al. ............... 264/127 |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,697,967 A | 12/1997 | Dinh et al. ............... 623/1 |
| 5,700,286 A | 12/1997 | Tartaglia ............... 623/1 |
| 5,707,385 A | 1/1998 | Williams ............... 606/192 |
| 5,711,763 A | 1/1998 | Nonami et al. |
| 5,713,949 A | 2/1998 | Jayaraman ............... 623/1 |
| 5,716,981 A | 2/1998 | Hunter et al. |
| 5,725,549 A | 3/1998 | Lam |
| 5,725,567 A | 3/1998 | Wolff et al. ............... 623/1 |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,746,691 A | 5/1998 | Frantzen ............... 600/36 |
| 5,755,771 A | 5/1998 | Penn et al. ............... 623/1 |
| 5,756,457 A | 5/1998 | Wang et al. |
| 5,756,476 A | 5/1998 | Epstein et al. |
| 5,759,192 A | 6/1998 | Saunders ............... 606/194 |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. ............... 428/36.1 |
| 5,769,883 A | 6/1998 | Buscemi et al. ............... 623/1 |
| 5,769,884 A | 6/1998 | Solovay |
| 5,780,807 A | 7/1998 | Saunders |
| 5,788,558 A | 8/1998 | Klein ............... 451/36 |
| 5,800,512 A | 9/1998 | Lentz et al. ............... 623/12 |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |

| | | | | | | |
|---|---|---|---|---|---|---|
| 5,836,962 | A | 11/1998 | Gianotti | 6,143,370 A | 11/2000 | Panagiotou et al. ......... 427/422 |
| 5,837,313 | A | 11/1998 | Ding et al. | 6,150,630 A | 11/2000 | Perry et al. |
| 5,837,835 | A | 11/1998 | Gryaznov et al. | 6,153,252 A | 11/2000 | Hossainy et al. |
| 5,840,083 | A | 11/1998 | Braach-Maksvytis | 6,159,951 A | 12/2000 | Karpeisky et al. |
| 5,843,172 | A | 12/1998 | Yan .................................... 623/1 | 6,160,084 A | 12/2000 | Langer et al. |
| 5,851,508 | A | 12/1998 | Greff et al. | 6,165,210 A | 12/2000 | Lau et al. ..................... 623/1.12 |
| 5,853,408 | A | 12/1998 | Muni | 6,165,212 A | 12/2000 | Dereume et al. |
| 5,854,207 | A | 12/1998 | Lee et al. | 6,166,130 A | 12/2000 | Rhee et al. |
| 5,855,612 | A | 1/1999 | Ohthuki et al. | 6,169,170 B1 | 1/2001 | Gryaznov et al. |
| 5,855,618 | A | 1/1999 | Patnaik et al. | 6,171,609 B1 | 1/2001 | Kunz |
| 5,856,814 | A | 1/1999 | Yagyu ............................. 345/89 | 6,174,330 B1 | 1/2001 | Stinson |
| 5,858,746 | A | 1/1999 | Hubbell et al. | 6,177,523 B1 | 1/2001 | Reich et al. |
| 5,865,814 | A | 2/1999 | Tuch | 6,183,505 B1 | 2/2001 | Mohn, Jr. et al. |
| 5,868,781 | A | 2/1999 | Killion | 6,187,045 B1 | 2/2001 | Fehring et al. |
| 5,873,904 | A | 2/1999 | Ragheb et al. ..................... 623/1 | 6,210,715 B1 | 4/2001 | Starling et al. |
| 5,874,101 | A | 2/1999 | Zhong et al. | 6,224,626 B1 | 5/2001 | Steinke |
| 5,874,109 | A | 2/1999 | Ducheyne et al. | 6,228,845 B1 | 5/2001 | Donovan et al. |
| 5,874,165 | A | 2/1999 | Drumheller | 6,240,616 B1 | 6/2001 | Yan ............................... 29/527.2 |
| 5,876,743 | A | 3/1999 | Ibsen et al. | 6,245,076 B1 | 6/2001 | Yan |
| 5,877,263 | A | 3/1999 | Patnaik et al. | 6,245,103 B1 | 6/2001 | Stinson |
| 5,879,398 | A | 3/1999 | Swarts et al. .................... 623/22 | 6,248,344 B1 | 6/2001 | Ylanen et al. |
| 5,879,713 | A | 3/1999 | Roth et al. | 6,251,135 B1 | 6/2001 | Stinson et al. |
| 5,888,533 | A | 3/1999 | Dunn | 6,251,142 B1 | 6/2001 | Bernacca et al. |
| 5,891,192 | A | 4/1999 | Murayama et al. | 6,273,913 B1 | 8/2001 | Wright et al. .................. 623/1.42 |
| 5,897,955 | A | 4/1999 | Drumheller | 6,281,262 B1 | 8/2001 | Shikinami |
| 5,906,759 | A | 5/1999 | Richter | 6,284,333 B1 | 9/2001 | Wang et al. |
| 5,914,182 | A | 6/1999 | Drumheller | 6,287,332 B1 | 9/2001 | Bolz et al. |
| 5,916,870 | A | 6/1999 | Lee et al. | 6,287,337 B1 | 9/2001 | Martakos et al. ............. 523/1.39 |
| 5,922,005 | A | 7/1999 | Richter et al. | 6,290,721 B1 | 9/2001 | Heath |
| 5,928,279 | A | 7/1999 | Shannon et al. .................... 623/1 | 6,293,966 B1 | 9/2001 | Frantzen |
| 5,942,209 | A | 8/1999 | Leavitt et al. | 6,303,901 B1 | 10/2001 | Perry et al. |
| 5,945,029 | A | 8/1999 | Scholz et al. ............ 252/62.9 R | 6,312,459 B1 | 11/2001 | Huang et al. |
| 5,948,428 | A | 9/1999 | Lee et al. | 6,327,772 B1 | 12/2001 | Zadno-Azizi et al. |
| 5,954,744 | A | 9/1999 | Phan et al. | 6,375,826 B1 | 4/2002 | Wang et al. |
| 5,957,975 | A | 9/1999 | Lafont et al. | 6,379,381 B1 | 4/2002 | Hossainy et al. ............. 623/1.42 |
| 5,965,720 | A | 10/1999 | Gryaznov et al. | 6,387,121 B1 | 5/2002 | Alt |
| 5,971,954 | A | 10/1999 | Conway et al. | 6,388,043 B1 | 5/2002 | Langer et al. |
| 5,972,027 | A | 10/1999 | Johnson ............................. 623/1 | 6,395,326 B1 | 5/2002 | Castro et al. |
| 5,976,182 | A | 11/1999 | Cox | 6,409,761 B1 | 6/2002 | Jang |
| 5,980,564 | A | 11/1999 | Stinson | 6,423,092 B2 | 7/2002 | Datta et al. |
| 5,980,928 | A | 11/1999 | Terry | 6,461,632 B1 | 10/2002 | Gogolewski |
| 5,980,972 | A | 11/1999 | Ding | 6,464,720 B2 | 10/2002 | Boatman et al. |
| 5,981,568 | A | 11/1999 | Kunz et al. | 6,479,565 B1 | 11/2002 | Stanley |
| 5,986,169 | A | 11/1999 | Gjunter | 6,485,512 B1 | 11/2002 | Cheng |
| 5,997,468 | A | 12/1999 | Wolff et al. | 6,492,615 B1 | 12/2002 | Flanagan |
| 6,010,445 | A | 1/2000 | Armini et al. | 6,494,908 B1 | 12/2002 | Huxel et al. |
| 6,010,529 | A | 1/2000 | Herweck et al. ................... 623/1 | 6,495,156 B2 | 12/2002 | Wenz et al. |
| 6,015,541 | A | 1/2000 | Greff et al. | 6,511,748 B1 | 1/2003 | Barrows |
| 6,027,779 | A | 2/2000 | Campbell et al. .......... 428/36.91 | 6,517,888 B1 | 2/2003 | Weber |
| 6,033,582 | A | 3/2000 | Lee et al. ......................... 216/37 | 6,527,801 B1 | 3/2003 | Dutta |
| 6,042,875 | A | 3/2000 | Ding et al. | 6,537,589 B1 | 3/2003 | Chae et al. |
| 6,048,964 | A | 4/2000 | Lee et al. | 6,539,607 B1 | 4/2003 | Fehring et al. |
| 6,051,648 | A | 4/2000 | Rhee et al. | 6,540,777 B2 | 4/2003 | Stenzel |
| 6,056,993 | A | 5/2000 | Leidner et al. | 6,554,854 B1 | 4/2003 | Flanagan |
| 6,060,451 | A | 5/2000 | DiMaio et al. | 6,565,599 B1 | 5/2003 | Hong et al. |
| 6,066,156 | A | 5/2000 | Yan | 6,569,191 B1 | 5/2003 | Hogan |
| 6,071,266 | A | 6/2000 | Kelley | 6,569,193 B1 | 5/2003 | Cox et al. |
| 6,074,659 | A | 6/2000 | Kunz et al. | 6,572,672 B2 | 6/2003 | Yadav et al. |
| 6,080,177 | A | 6/2000 | Igaki et al. | 6,574,851 B1 | 6/2003 | Mirizzi |
| 6,080,488 | A | 6/2000 | Hostettler et al. | 6,585,755 B2 | 7/2003 | Jackson et al. |
| 6,083,258 | A | 7/2000 | Yadav | 6,592,614 B2 | 7/2003 | Lenker et al. |
| 6,093,463 | A | 7/2000 | Thakrar | 6,592,617 B2 | 7/2003 | Thompson |
| 6,095,817 | A | 8/2000 | Wagner et al. ................. 433/173 | 6,610,087 B1 | 8/2003 | Zarbatany et al. ............. 623/1.32 |
| 6,096,070 | A | 8/2000 | Ragheb et al. | 6,613,072 B2 | 9/2003 | Lau et al. |
| 6,096,525 | A | 8/2000 | Patnaik | 6,626,939 B1 | 9/2003 | Burnside et al. |
| 6,099,562 | A | * 8/2000 | Ding et al. .................... 623/1.46 | 6,635,269 B1 | 10/2003 | Jennissen |
| 6,103,230 | A | 8/2000 | Billiar et al. | 6,645,243 B2 | 11/2003 | Vallana et al. |
| 6,107,416 | A | 8/2000 | Patnaik et al. | 6,656,162 B2 | 12/2003 | Santini, Jr. et al. |
| 6,110,188 | A | 8/2000 | Narciso, Jr. | 6,664,335 B2 | 12/2003 | Krishnan |
| 6,113,629 | A | 9/2000 | Ken | 6,666,214 B2 | 12/2003 | Canham |
| 6,117,979 | A | 9/2000 | Hendriks et al. | 6,667,049 B2 | 12/2003 | Janas et al. |
| 6,120,536 | A | 9/2000 | Ding et al. | 6,669,723 B2 | 12/2003 | Killion et al. |
| 6,120,904 | A | 9/2000 | Hostettler et al. | 6,676,697 B1 | 1/2004 | Richter |
| 6,121,027 | A | 9/2000 | Clapper et al. | 6,679,980 B1 | 1/2004 | Andreacchi |
| 6,125,523 | A | 10/2000 | Brown et al. | 6,689,375 B1 | 2/2004 | Wahlig et al. |
| 6,127,173 | A | 10/2000 | Eckstein et al. | 6,695,920 B1 | 2/2004 | Pacetti et al. |
| 6,129,761 | A | 10/2000 | Hubbell | 6,706,273 B1 | 3/2004 | Roessler |
| 6,129,928 | A | 10/2000 | Sarangapani et al. | 6,709,379 B1 | 3/2004 | Brandau et al. |
| 6,139,573 | A | * 10/2000 | Sogard et al. ................. 623/1.13 | 6,719,934 B2 | 4/2004 | Stinson |

| | | |
|---|---|---|
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0038145 A1 | 3/2002 | Jang ............... 623/1.15 |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | DiMatteo et al. |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 687 008 | 12/1995 |
| EP | 0 709 068 | 5/1996 |
| EP | 0 970 711 | 1/2000 |
| GB | 2 247 696 | 3/1992 |
| JP | 63-160645 | 7/1988 |
| JP | 3-14516 | 1/1991 |
| JP | 4-215768 | 8/1992 |
| JP | 8-33718 | 2/1996 |
| JP | 8-213026 | 8/1996 |
| JP | 9-85028 | 3/1997 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/13268 | 6/1994 |
| WO | WO 94/21196 | 9/1994 |
| WO | WO 95/11817 | 5/1995 |
| WO | WO 95/29647 | 11/1995 |
| WO | WO 96/28115 | 9/1996 |
| WO | WO 98/04415 | 2/1998 |
| WO | WO 98/23228 | 6/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J Applied Polymer Sci, 38, pp. 55-64(1984).

Kelley et al., *Totally Resorbable High-Strength Composite Material*, Advances in Biomedical Polymers, 35, pp. 75-85 (1987).

Kubies et al., *Microdomain Structure in polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents pp. 1-16 (1999).

Mauduit et al., *Hydrolytic degradation of films prepared from blends of high and low molecular weight poly(DL-lactic acid)s*, J. Biomed. Mater. Res. v. 30, pp. 201-207 (1996).

Martin et al., *Enhancing the biological activity of immobilized osteopontin using a type-1 collagen affinity coating*, J. Biomed. Mater Res 70A, pp. 10-19 (2004).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569. (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports 3, pp. 10-17 (2001).

Völkel et al., *Targeting of immunoliposomes to endothelial cells using a single—chain Fv fragment directed against human endoglin (CD105)*, Biochimica et Biophysica Acta 1663, pp. 158-166 (2004).

Yau et al., Modem Size-Exclusion Liquid Chromatography, Wiley-Interscience Publication, IX-XV (1979).

Lambert et al., *Localized Arterial Wall Drug Delivery From a Polymer-Coated Removable Metallic Stent*, Circulation 90(2):1003-1011 (Aug. 1994).

De Scheerder et al., *Biocompatibility of Polymer-Coated Oversized Metallic Stents Implanted in Normal Porcine Coronary Arteries*, Atherosclerosis 114:105-114 (1995).

* cited by examiner

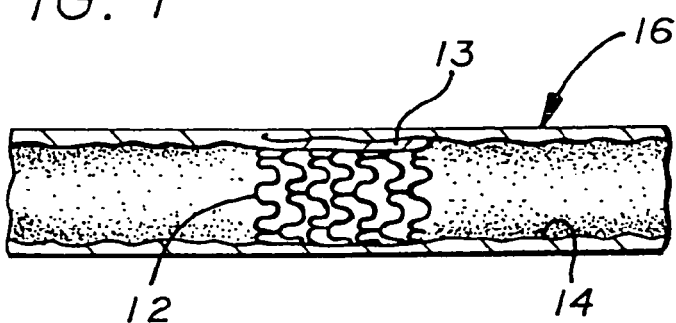
FIG. 1
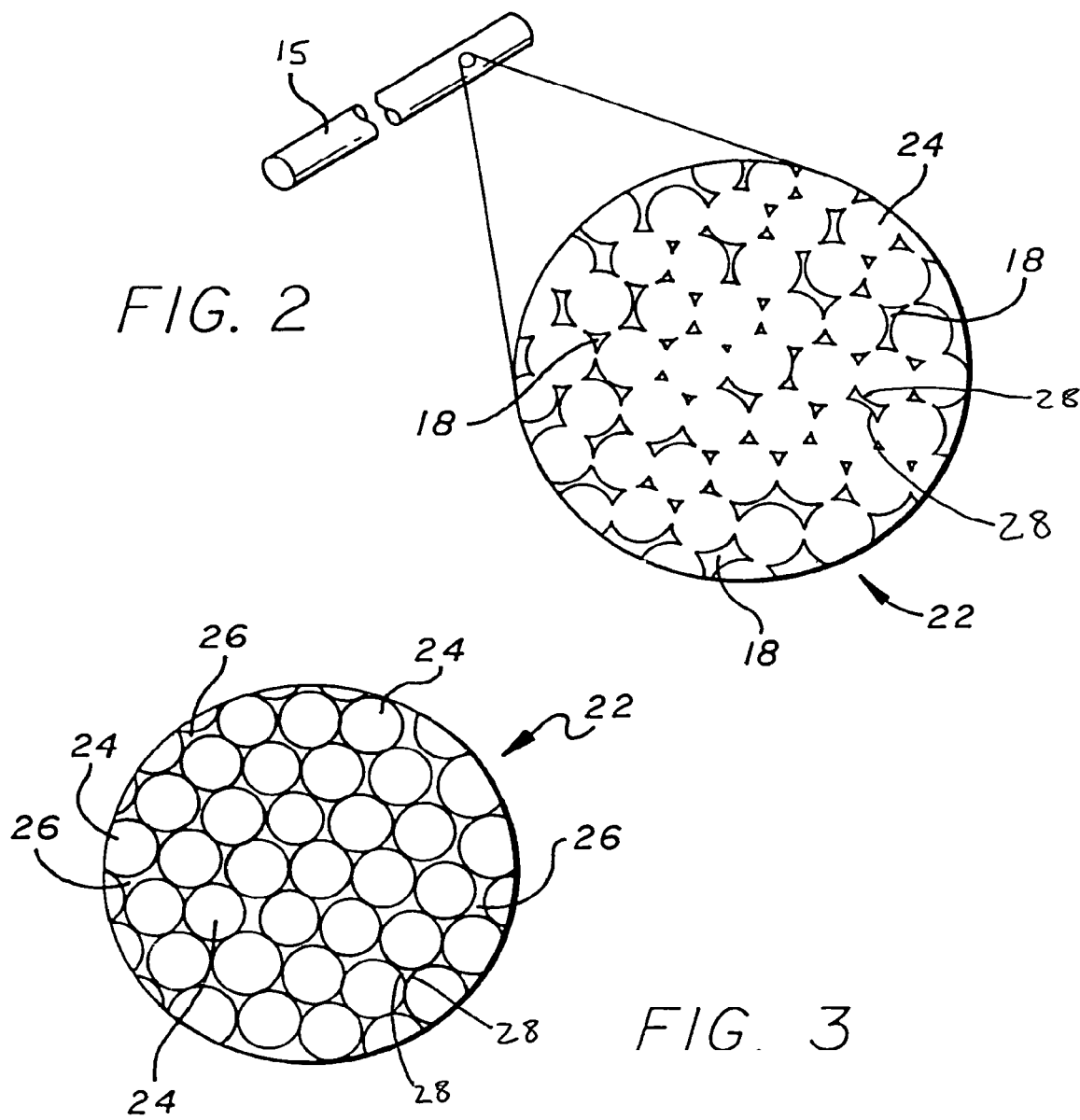
FIG. 2
FIG. 3

MEDICATED POROUS METAL PROSTHESIS

CROSS REFERENCE

This application is a divisional of currently pending U.S. patent application Ser. No. 10/767,296, filed Jan. 28, 2004; which is a divisional of application Ser. No. 10/235,033, which was filed on Sep. 3, 2003, U.S. Pat. No. 6,723,120, issued on Apr. 20, 2004; which is a continuation of application Ser. No. 09/797,313, filed on Mar. 1, 2001 and abandoned on Oct. 11, 2002; which is a divisional of application Ser. No. 08/837,993, filed on Apr. 15, 1997, U.S. Pat. No. 6,240,616, issued on Jun. 5, 2001.

FIELD OF THE INVENTION

This invention generally relates to a medicated prosthesis or implant, and a method of making the same. More particularly, the invention relates to a porous prosthesis, such as a stent, that can be planted in the vasculature of a patient and can deliver a therapeutic agent to the site of implantation.

DESCRIPTION OF RELATED ART

Stents are generally cylindrically shaped prosthetic implants which function to hold open and sometimes expand a segment of a blood vessel or other anatomical lumen. They are particularly suitable for supporting and preventing a torn or injured arterial lining from occluding a fluid passageway. Intravascular stents are very useful for treatment of coronary artery stenoses, and for reducing the likelihood of the development of restenosis or closure after balloon angioplasty.

The success of a stent can be assessed by evaluating a number of factors, such as the degree of development of thrombosis; degree of neointimal hyperplasia or smooth muscle cell migration and proliferation following implantation of the stent; severity of injury to the artery wall; overall loss of luminal patency; stent diameter in vivo; thickness of the stent; and leukocyte adhesion to the luminal lining of stented arteries. However, the chief areas of concern are early subacute thrombosis, and eventual restenosis of the blood vessel due to intimal hyperplasia.

Therapeutic pharmacological agents have been developed to improve successful placement of the stent and are delivered to the site of stent implantation. Stents that are of a common metallic structure were previously unable to deliver localized therapeutic pharmacological agents to a blood vessel at the location being treated with the stent. There are polymeric materials that can be loaded with and release therapeutic agents. However, these polymeric materials may not fulfill the structural and mechanical requirements of a stent, especially when the polymeric materials are loaded with a drug, since drug loading of a polymeric material can significantly reduce the structural and mechanical properties of the polymeric material.

It has been known in the art to coat a metallic stent with a polymeric material and load the polymeric material with a drug. Alternatively, stents of polymeric materials have been reinforced with metal structure. These stent designs have the strength necessary to hold open the lumen of the vessel because of the reinforced strength of the metal. Stents made of both polymeric material and metal have a larger radial profile because the volume occupied by the metal portion of the stent cannot absorb and retain drugs. Reducing the profile of a stent is preferable because it increases the in vivo diameter of the lumen created by the stent. Thus it is desirable to configure a metallic stent to deliver drugs to the blood vessel walls without substantially increasing the profile of the stent. The present invention meets these needs.

SUMMARY

In an aspect of the present invention, a method of manufacturing a stent is provided, including attaching a first group of particles together to form a first porous network; and attaching a second group of particles together and to the first porous network to form a second porous network, wherein the average particle size of the first group is greater than the average particle size of the second group so that the first porous network has an average pore size that is greater than the average pore size of the second porous network. In one embodiment, the method additionally includes depositing a therapeutic substance in the first porous network, wherein the second porous network reduces the rate of release of the substance from the stent after the stent has been implanted in a body of a patient. In another embodiment, the method further includes depositing a polymeric film layer on the second porous network. In a further embodiment, the particles of the second group are attached all the way around the first porous network such that the second porous network completely surrounds the first porous network.

In another aspect of the invention, a method of manufacturing a stent is provided, including sintering elongated fibers together to form a component of a stent body.

In a further aspect, a method of manufacturing a stent is provided including forming a first porous region; forming a second porous region disposed over a portion of the first porous region; and depositing a therapeutic substance in the first porous region, wherein an average pore size of the second porous region is less than an average pore size of the first porous region. In one embodiment, the second porous region is for contacting the wall of a vessel when the stent has been implanted in the vessel. In another embodiment, the method further includes forming a third porous region over a portion of the first porous region such that the first porous region is between the second and third porous regions. In a further embodiment, the first or second porous region is formed by sintering particles. In yet another embodiment, the first porous region is formed by sintering particles having a first average diameter, and the second porous region is formed by sintering particles having a second average diameter, wherein the first average diameter is larger than the second average diameter.

In another aspect, a method of manufacturing a stent is provided, including forming a first porous region; forming a second porous region disposed over a first portion of the first porous region; forming a third porous region disposed over a second portion of the first porous region; and depositing a therapeutic substance in the first porous region; and wherein an average pore size of the second porous region and an average pore size of the third porous region is less than an average pore size of the first porous region for reducing a rate of release of the therapeutic substance from the first porous region after the stent has been implanted in a vessel.

In yet a further aspect, a method of manufacturing a strut element for a stent is provided, including placing metallic particles having an average first diameter in contact with each other; sintering the metallic particles having the average first diameter to form an inner core; placing metallic particles having an average second diameter on the inner core; and sintering the metallic particles having the average second diameter to form a porous outer layer. In one embodiment, the average second diameter is less than the average first diameter. In another embodiment, the method further includes depositing a therapeutic substance in the inner core.

In another aspect, a stent is provided including a strut element wherein the strut element includes a solid metallic inner core and an outer layer disposed over the inner core, the outer layer being made from a porous metallic material. In one embodiment, the porous metallic material is made from sintered particles, filaments or fibers. In another embodiment, the outer layer is capable of holding a therapeutic substance for releasing of the substance after the stent has been implanted in a vessel.

In yet a further embodiment, a stent is provided including a solid metallic region and a porous metallic region disposed on the solid metallic region. In one embodiment, the porous metallic region is made from sintered particles, filaments or fibers.

In another embodiment, a method of manufacturing a strut element for a stent is provided, including applying metallic particles onto a solid inner core; and sintering the metallic particles to form a porous outer layer disposed over a portion of the solid inner core.

In a further aspect of the present invention, a method of manufacturing a sintered sheet element for a stent is provided, including placing metallic particles having an average first diameter to a first surface of a metallic core layer; placing metallic particles having an average second diameter to a second surface of the metallic core layer; sintering the metallic particles having the average first diameter to form a first porous outer layer; and sintering the metallic particles having the average second diameter to form a second porous outer layer. In one embodiment, the first and second porous outer layers are on opposing sides of the metallic core layer. In another embodiment, the metallic core layer is a porous substrate. In yet another embodiment, the metallic core layer is a solid substrate. In a further embodiment, the method additionally includes applying a therapeutic agent to the first porous outer layer or the second porous outer layer after the formation of the first and second porous outer layers.

BRIEF DESCRIPTION OF THE DRAWINGS

FIG. 1 is a longitudinal sectional view of a blood vessel with a stent manufactured according to one embodiment of the present invention.

FIG. 2 is a magnified, partially cut away perspective view of a porous stent wire or strut manufactured according to one embodiment of the present invention.

FIG. 3 is a magnified, cross-sectional view of unsintered packed particles.

DETAILED DESCRIPTION

Figure 5:
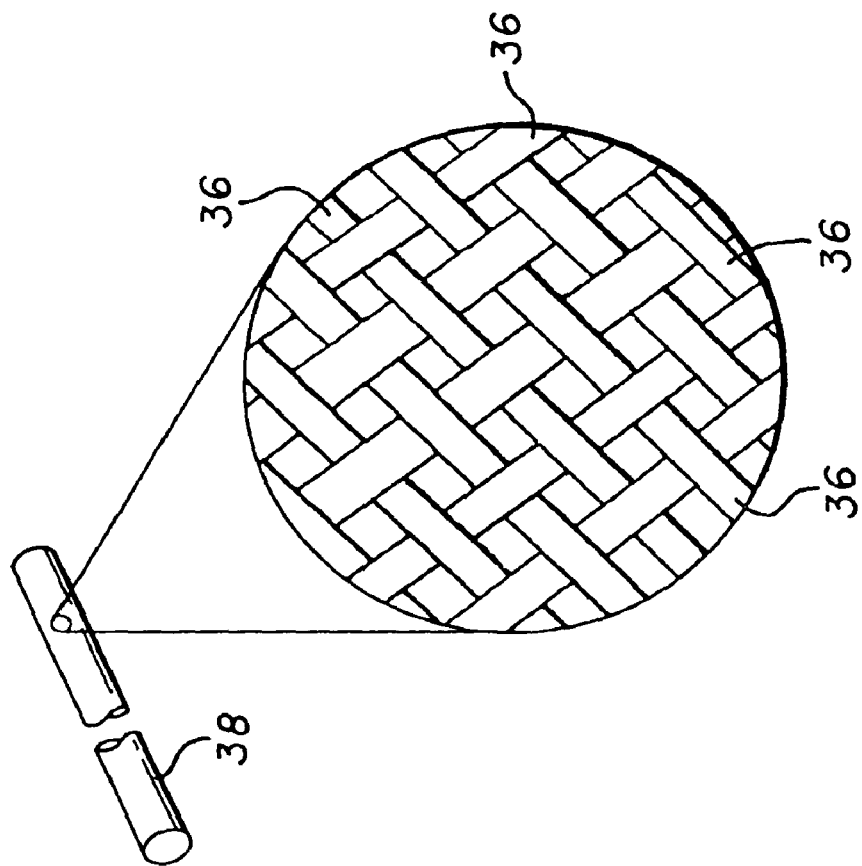
FIG. 5 is a porous stent wire or strut in partially magnified, partially cut away perspective manufactured according to one embodiment of the present invention.

Referring now to FIG. 1, the prosthesis of one embodiment is a porous stent 12 that is radially expandable against a wall 14 of a vessel 16. The stent 12 is loaded with a therapeutic agent in porous cavities or pores 18 (FIG. 2) of the stent 12. When placed in the vasculature, the therapeutic agent is delivered to the tissue that comes into contact with the stent 12. The stent 12 of one preferred embodiment is formed of a stent wire 15 that is porous. An example of the wire 15 is a sintered metal wire. FIG. 2 illustrates a partial microscopic view of the sintered wire 15 that is suitable for use in one embodiment of the present invention. The wire 15 has porous cavities 18. The size of the cavities or pores 18 preferably ranges between 0.01 and 20 microns.

Porous metal is made, according to one preferred embodiment, by the process of sintering metal. Sintering is a process where particles 24 are bonded together without entirely melting the particles 24. The particles 24 are pressed together or molded into a desired shape. A considerable amount of pressure is first applied to press the particles 24 together. The metal is then heated to temperatures slightly below the melting point of the metal. Without entirely melting, the particles 24 bond to each other at their respective surfaces. Space remains between a lattice 22 of the particles 24 which define the cavities or pores 18.

The formation of sintered metal is illustrated with reference to FIG. 3 and continued reference to FIG. 2. FIG. 3 is a microscopic view of a packed lattice 22 of the metallic particles 24. Gaps 26 exist between each particle 24 despite the fact that the particles 24 are pressurized and are in contact with adjacent particles 24. The particles 24 are preferably sized between 0.02 microns (6 nm) and 20 microns (0.5 μm) in diameter. Prior to heating, there are no chemical bonds formed between the individual particles 24. When the metal is heated to slightly below the melting point of the metal, the particles 24 bond with neighboring particles 24. The gaps 26 in the packed lattice 22 form pores 18 when the particles 24 are sintered. Thus in FIG. 2, the metal stent wire 15 formed by the process of sintering has the porous cavities 18 extending throughout the entire wire 15, thereby interconnecting the cavities 18. The cavities 18 then can be filled with a therapeutic agent as hereinafter described. The appropriate pressure and temperature of sintering a particular metal is specific to that particular metal. One skilled in the art of metal fabrication understands how to sinter any given metal or alloy.

For each of the embodiments, the metal stent material can be any suitable metal such as stainless steel, tantalum, nickel-titanium alloy, platinum-iridium alloy, molybdenum-rhenium alloy, gold, magnesium, or combinations thereof, although other similar materials also may be suitable. The metal can be modified to exhibit different hardnesses, and thus varying stiffnesses, by well known annealing and manufacturing processes.

One of the most important factors to be considered when making a stent according to one embodiment of the present invention is the porosity of the metal. Porosity is the total volume of pores in the sintered metal divided by the total volume of the metal. Porosity determines the amount of a therapeutic agent that can be loaded into the stent 12 of predetermined dimensions. High porosity means that the stent 12 can deliver more therapeutic agents or have a narrower profile because the stent 12 is less dense. High porosity, according to some embodiments of the present invention, adversely affects the strength and elasticity of a metal. Consequently, there is an ongoing tradeoff between stent strength, on the one hand, and stent profile and stent load capacity on the other hand.

Pore size is a function of particle size and dimension. In one embodiment of the present invention illustrated in FIG. 3, the particles 24 are generally spherical. Size of the pores 18, particularly with generally spherical particles 24, is proportional to particle size. When the particles 24 have inconsistent size, smaller particles tend to fill the gaps 26 between the larger particles 24. Thus, the porosity of such particles 24 is less predictable. Consistent pore size is also important to ensure that drugs are evenly distributed throughout the stent 12. Consistent distribution on the other hand ensures that the tissue in contact with the stent 12 will receive an even distribution of the therapeutic agent.

There are several types of drugs that can be administered by the stent 12 when placed in the vessel. Examples of therapeutic drugs, or agents include antiplatelets, antifibrins, antithrombins and antiproliferatives. Examples of anticoagulants, antiplatelets, antifibrins, and antithrombins include but are not limited to sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen, Inc., Cambridge, Mass.), and 7E-3B® (an antiplatelet drug from Centocore, Inc., Mavern, Pa.). Examples of cytostatic or antiproliferative agents include angiopeptin (a somatostatin analogue from Beaufour Ipsen S. A., Paris, France), angiotensin converting enzyme inhibitors such as Captopril® (available from Bristol-Myers Squibb Co., New York, N.Y.), Cilazapril® (available from Hoffmann-La Roche Inc., Nutley, N.J.), or Lisinopril® (available from Merck & Co., Inc., Whitehouse Station, N.J.), calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck & Co., Inc.), methotrexate, monoclonal antibodies (such as to PDGF receptors), nitroprusside, phosphodiesterase inhibitors, prostaglandin inhibitor (available from GlaxoSmithKline plc, Middlesex, United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon and genetically engineered epithelial cells, for example.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agent are known in the art. Furthermore, the calculation of dosages, dosage rates and appropriate duration of treatment are previously known in the art.

The therapeutic agent of one embodiment is preferably in liquid form and is loaded into the stent 12 by immersing the stent 12 in a medicated solution. The therapeutic agent may be dissolved in a solvent or suspended in a liquid mixture. If a suspension of drugs is used, it is important that the pore size of the stent 12 is considerably larger than the therapeutic agent. An average pore size that is more than ten (10) times the particle size of a suspended therapeutic agent is suitable. After the stent 12 is immersed in the medicated solution, the therapeutic agent absorbs into the pores of the stent 12. At which time, the loaded stent 12 can be removed from the solution and implanted into the vasculature of a patient. Additionally, a therapeutic agent can be loaded into the stent 12 by applying pressure to the fluid to aid the passage of the medicated fluid into the pores 18 of the stent 12. This can be done similar to how fluid can be pressurized through the pores of a filter.

Once loaded, the therapeutic agent remains in place by the surface tension between walls 28 of the several porous cavities 18 and the therapeutic agent. As shown in FIG. 1, the loaded or medicated stent 12 is then deployed to the site of arterial closure 13 and is expanded. The expanded stent 12 engages the walls 14 of the vessel 16 to maintain the patency of the vessel 16. Once in the vessel 16, the therapeutic agent disseminates from the porous cavities 18 of the stent 12 and is absorbed into the tissue of the walls 14 of the vessel 16 that are in contact with the stent 12.

The advantage of the stent 12 of the present invention over prior art medicated stents is one of profile and strength. Metal, including sintered metal, is stronger than synthetic materials that are capable of being loaded with a therapeutic agent. Thus, in order for a medicated stent to deliver an appropriate amount of a therapeutic agent and structurally maintain vessel patency, the profile of the stent must be substantially larger than metal stents. This is true whether a metal stent is coated with a therapeutic agent, or if the stent is entirely made of a plastic material.

Sintered metal has strength and elasticity that is comparable to regular metal. Sintered metal furthermore has the added feature that it is porous. Consequently, a sintered stent can be made having a profile that is substantially comparable to a conventional metal stent. Yet, a therapeutic agent can be loaded into the pores and delivered to the site of stent implantation without the aid of medicated coatings.

Additionally, many synthetic materials, including materials that are bioabsorbable, cause inflammation of the tissue. A medicated stent that has a therapeutic agent loaded directly into the pores 18 of the stent 12 can avoid synthetic coatings that have been known to cause irritation at the site of stent implantation.

Figure 4:
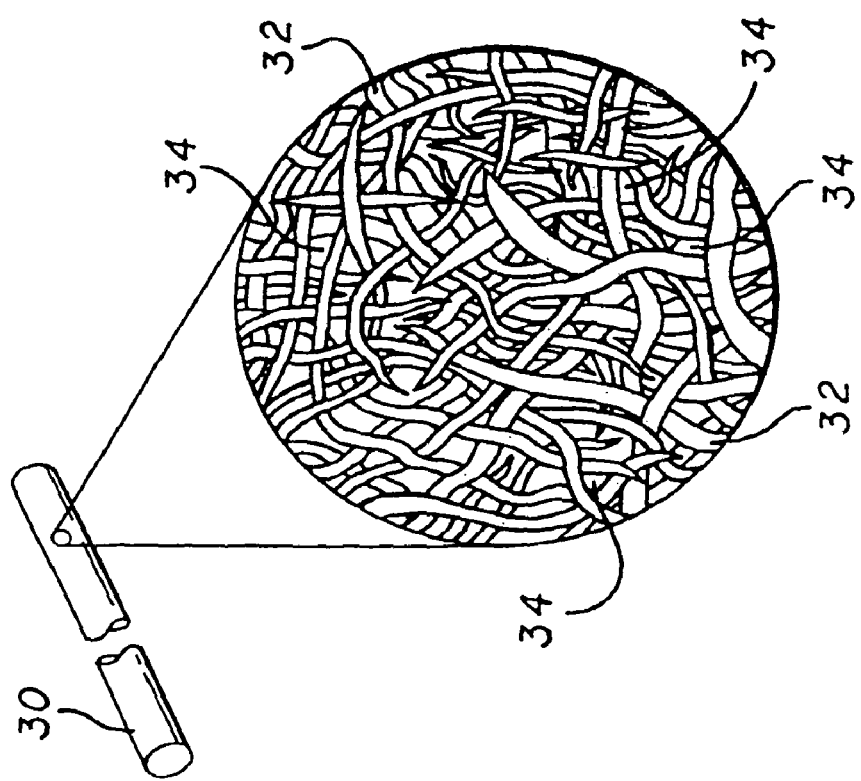
FIG. 4 is a porous stent wire or strut in partially magnified, partially cut away perspective manufactured according to one embodiment of the present invention.

FIG. 4 illustrates an alternative embodiment of a stent wire 30 constructed according to the present invention. The stent 12 is formed of elongated particles, i.e., filaments or fibers 32. Sintered particles 24 that are generally spherical in shape are capable of forming sintered metal having a porosity in the range of 0.30 to 0.05. However, when filaments or fibers 32 are sintered, the porosity can be increased above 0.30. The technique of fabricating a stent with elongated filaments or fibers 32 is similar to the method described above for spherical particles 24 or powders. The filaments or fibers 32 are molded and pressurized. Then the filaments or fibers 32 are heated to a temperature just below the melting point of the metal.

Greater porosity of the stent 12 made of metal filaments or fibers 32, rather than spherical particles 24, is obtained because of the irregular shape of the filaments or fibers 32. The filaments or fibers 32 cannot be packed as tightly as regular generally spherical particles 24. Furthermore, the filaments or fibers 32 can be packed less densely and still maintain contact between the filaments or fibers 32 to allow sintering. Thus, the void space or pores 34 in the sintered metal are larger.

The strength of the stent wire 30 using filaments or fibers 32 in FIG. 4 is improved because the individual strands have larger surface area to volume and contact a greater number of neighboring strands. Thus, each filament or fiber 32 will have a larger bonding surface and may bond with a greater number of neighboring filaments or fibers 32. A matrix of overlapping filaments or fibers 32 is thus formed with greater porosity and stronger inter-particle bonding.

In yet another embodiment, wire fibers 36 are woven or twined into a structure 38 as illustrated in FIG. 5. The individual strands cooperate in a synergistic manner to reinforce the strength of the wire 38. Additionally, the wire fibers 36 can be woven into the form of a sintered metal sheet having improved and reinforced strength or a sintered metal tube. Other combinations of particle size and shape can be employed to form a stent wire having different characteristics.

Figure 6:
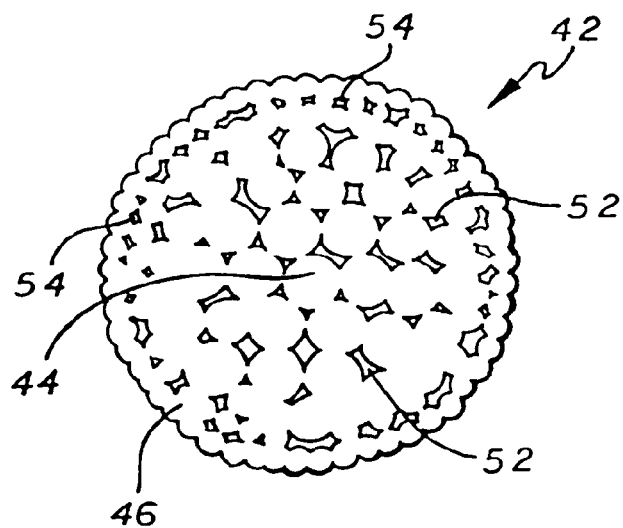
FIG. 6 is a cross-sectional view of a stent wire or strut manufactured according to one embodiment of the present invention.

In another embodiment illustrated in FIG. 6, a stent wire 42 is formed of an inner core 44 and an outer layer or core 46 of the particles 24. The outer layer 46 is formed from the particles 24 having a different diameter than the diameter of the particles 24 that form the inner core 44. For example, the core 44 of the metal is formed of particles that have a diameter in the range of 10-20 microns at the core of the wire 42. Surrounding the core 44 are particles that have a diameter in the range of 2-4 microns on the outer layer 46. The larger particles create the core 44 having larger pores 52. This results in higher porosity and thus a higher load capacity. The smaller particles on the outer layer 46 form smaller pores 54 which reduce the rate of diffusion of drugs into the tissues of a vessel.

When a therapeutic agent is loaded into the stent 12 formed of the wire 42 illustrated in FIG. 6, a larger volume can be stored in the larger pores 52 at the core 44 of the wire 42. Once the stent 12 is placed into a vessel, the therapeutic agent in the stent wire 42 is delivered at a rate determined by the smaller pores 54 in the outer layer 46 of the stent wire 42. Such a structure is expected to have a benefit of being able to store a large amount of a therapeutic agent at the core 44 and deliver the therapeutic agent at a slower rate. Consequently, this design is desirable for low-dose, long-term drug therapy.

Figure 7:
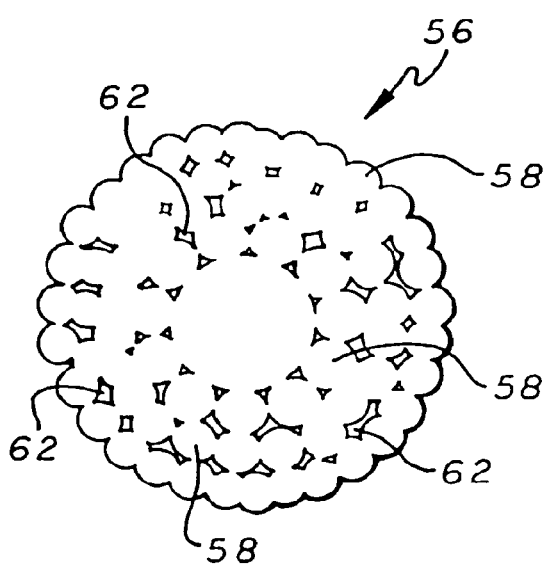
FIG. 7 is a cross-sectional view of a stent wire or strut manufactured according to one embodiment of the present invention.

Alternatively, according to another embodiment of the present invention shown in FIG. 7, a stent wire 56 is formed from sintered metal particles 58. The pores 62 formed between the sintered particles 58 surrounding a solid core retain the therapeutic agent. The total porosity of the stent wire 56 having the solid core and porous outer layer is much lower than a stent wire of similar proportion that is entirely made of sintered particles. However, the solid core reinforces the tensile strength and elasticity of the metal stent and is considerably stronger. Thus, it is desirable to use a sintered stent with a solid core for applications where maximum tensile strength and elasticity is desirable and only a relatively small amount of therapeutic agent is needed.

Figure 8:
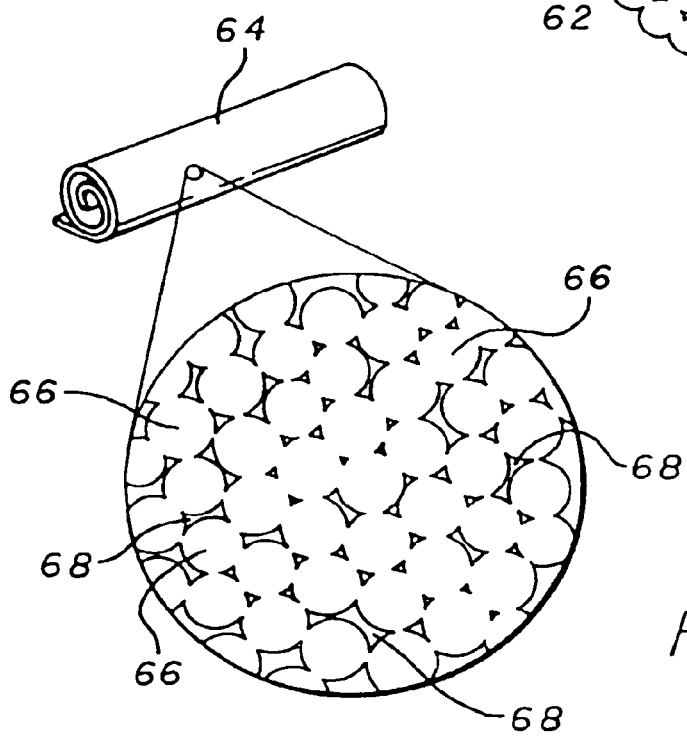
FIG. 8 is a partially magnified perspective of a stent formed from a sheet of sintered metal according to one embodiment of the present invention.

The sintered metal stent of yet another embodiment of the present invention can be made of material formed in different shapes than sintered metal. For example, the stent can be formed of a sheet of sintered metal as shown in FIG. 8 or a sintered metal tube 64. By way of example, metal particles 66 are arranged and pressurized into the sheet 64. The sheet 64 is heated to a temperature below the melting point of the particles 66 as described previously. The sheet 64 of sintered metal is porous as illustrated by reference number 68.

The same principles that apply to porosity and pore size of a wire apply equally to a sintered stent that is formed into a sheet or tube. The advantage of forming the stent from a sheet of metal is that the stent is radially expandable without placing a great deal of strain on the metal lattice when it is expanded. A sheet or tube of sintered metal can be cut in the desired shape to form the metal structural member with a laser, such as a continuous $CO_2$ laser, a pulsed YAG laser, or an excimer laser, for example, or alternatively, by chemical etching or stamping. When cut from a flat sheet, the stent is then rolled into a cylindrical configuration and laser welded along the longitudinal edges.

Figure 9:
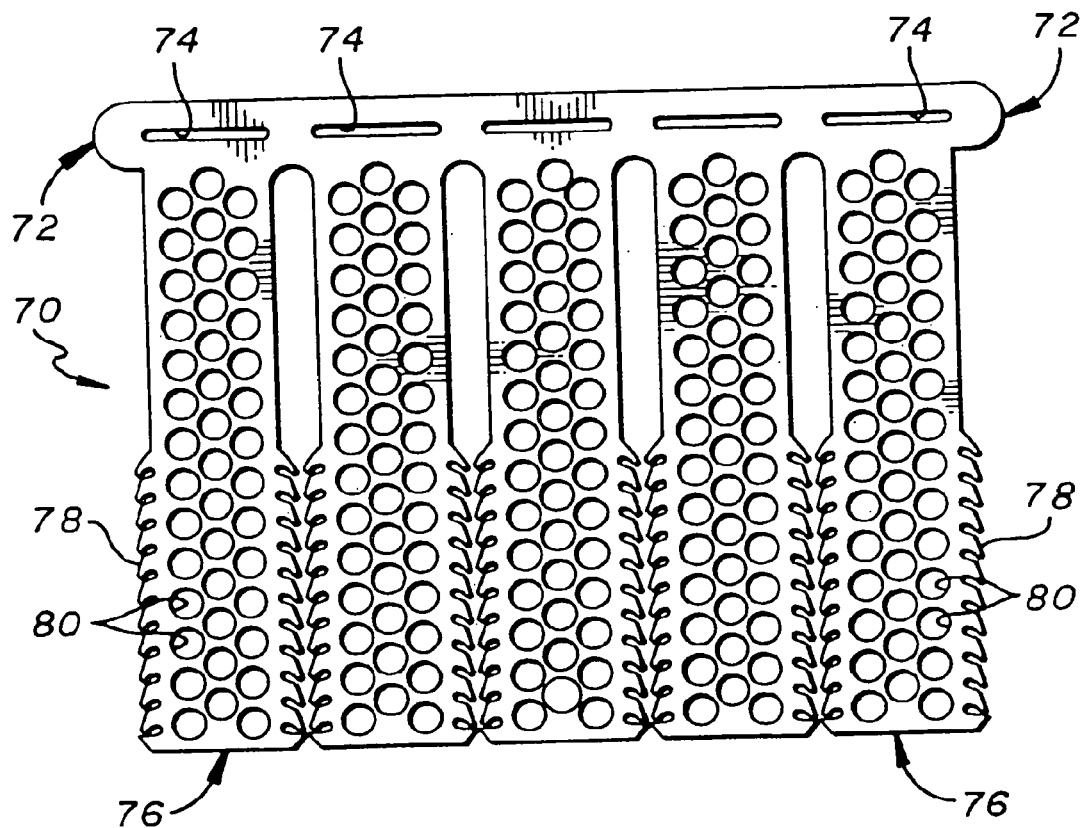
FIG. 9 is a sheet of sintered metal manufactured according to one embodiment of the present invention.

The stent can be formed into any particular pattern. One such pattern is a rolled locking design and is illustrated in FIG. 9. A sheet 70 is etched into a configuration that has a head portion 72 that includes one or more slots 74 for receipt of a like number of tail portions 76. The tail portions 76 are received into the slots 74 so as to form a cylindrical loop. The tail portions 76 include a plurality of teeth 78 adapted to cooperatively engage the slots 74 of the head portion 72. When the teeth 78 engage the slots 74, the tail portions 76 are retained in place in an expanded state. Additionally, holes 80 are formed throughout the stent to reduce the metal to air ratio of the stent. The less metal in contact with the wall of the vessel, the better the blood compatibility of the stent.

Prior to deployment, the tail portions 76 are coiled into a retracted position. The tail portions 76 are threaded through the slots 74 and wound. The stent is expanded by a balloon according to principles that are well known in the art for delivering and implanting a stent. As the stent is expanded by a balloon during deployment, the stent unwinds and the teeth 78 lock into the slots 74 at a desired radial diameter to prevent the stent from returning to its original retracted state.

A benefit of the coiled stent shown in FIG. 9 is that the stent can be etched to have a minimal surface area that comes in contact with the walls of the vessel. This may be an important feature when it is desired to cover an entire portion of the walls of a blood vessel with a therapeutic agent because the coiled sheet metal stent can be configured to maintain maximum surface area contact with the wall of the blood vessel in contrast to wire stents.

Figure 10:
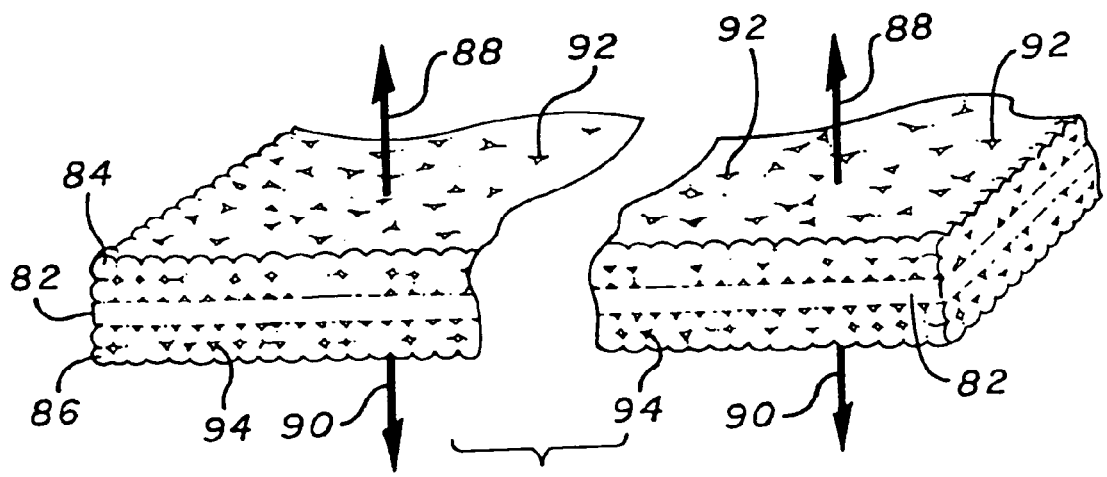
FIG. 10 is a cross-sectional, partially cut away view of a sheet of sintered metal manufactured according to the principles of one embodiment of the present invention.

With reference to FIG. 10, another embodiment of the present invention is a sheet formed of sintered particles that are sintered to top and bottom sides 84 and 86 of a metal sheet 82. The sheet 82 of FIG. 10 is similar in structure to the stent wire 56 of FIG. 7 that has the solid core and has porous particles sintered to the core forming a porous outer layer. The solid core reinforces the strength of the metal. The metal sheet 82 also provides a barrier through which a therapeutic agent cannot pass. Thus, a therapeutic agent loaded into the pores 92 on the top side 84 of the sheet 82 permeates in a first direction 88 outward from the solid core. A therapeutic agent loaded into the pores 94 on the bottom side 86 of the solid core permeates only in a second direction 90 opposite to the direction of the therapeutic agent loaded into the pores 92 on the top side 84.

When a stent made of the sheet of FIG. 10 is looped into a cylindrical formation and placed into a vessel, only the top side 84, which is directed radially outward, engages the wall of the vessel. The bottom side 94 faces radially inward and does not come in contact with the wall of the vessel. Thus, if it is desired, a first therapeutic agent can be loaded into the top side 84 to treat the tissues of the wall of the vessel. A second therapeutic agent can be loaded into the bottom side 86 to prevent coagulation of the blood flowing in the vessel. Additionally, the stent can be formed so that the particles are sintered only to one side 84 or 86 of the stent. A therapeutic agent is loaded into the sintered metal on the porous side 84 or 86 of the stent. When a stent is formed from a one-sided porous sheet, the porous side can be oriented radially outward to deliver a therapeutic agent to the tissues of the wall of the vessel.

Figure 11:
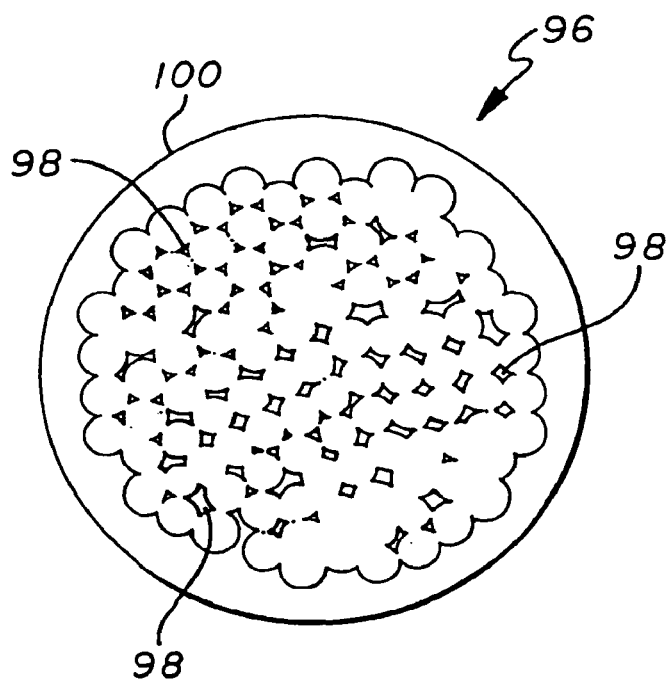
FIG. 11 is a cross-sectional view of a stent wire or strut manufactured according to the principles of one embodiment of the present invention.

FIG. 11 illustrates a cross-sectional view of a stent wire 96 according to another embodiment of the invention. The stent wire 96 has a plurality of porous cavities or pores 98. A therapeutic agent is loaded into the pores 98 of the sintered metal. Then, a coating 100 is applied to the sintered metal. The coating 100 may be used for several purposes as illustrated hereinafter.

Figure 12:
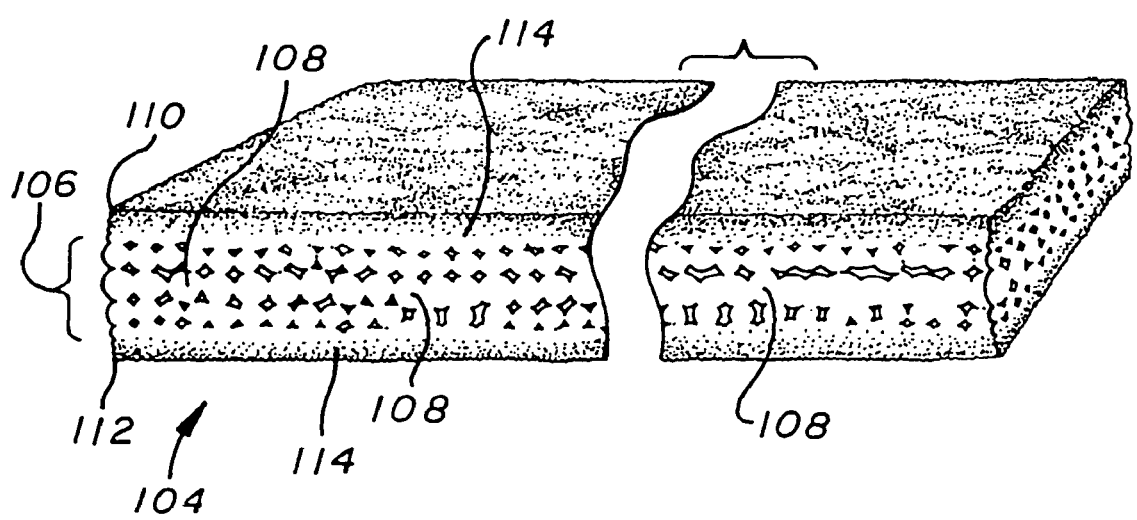
FIG. 12 is a cross-sectional view, partially cut away of a sheet of sintered metal manufactured according to the principles of one embodiment of the present invention.

With reference to FIG. 12, another embodiment of the invention is shown wherein the stent is formed of a sintered sheet 104 of metal having a middle core layer 106 formed of large diameter particles 108 that form large pores. The core layer 106 is sandwiched between top and bottom layers 110 and 112 formed of smaller diameter particles 114 or particles that form smaller diameter pores. The sheet 104 is formed by orienting the core layer 106 of the large diameter particles 108 along a plane. The top layer 110 of smaller diameter particles 114 is arranged in a plane parallel to and above the core middle layer 106. The bottom layer 112 of the particles 114 is arranged in a plane parallel to and below the core middle layer 106. The three layers 106, 110, and 112 are pressed together and sintered into the single sheet 104. The sheet 104 can then be cut or etched into a stent configuration.

While one of the benefits of the present invention is to provide a stent that does not require a coating for the purpose of delivering a therapeutic agent, the application of a coating after a therapeutic agent is loaded into the pores of the sintered metal does not defeat the utility of the present invention. For example, when a therapeutic agent is loaded into the pores of the stent and into a polymeric coating, the profile of the polymeric coating can be reduced. Alternatively, a larger dosage of a therapeutic agent can be delivered to the site of stent implantation. Additional benefits are observed by loading a stent with a therapeutic agent in the pores of the metal and then further applying a coating to the stent. Furthermore, even if a coating is applied to the stent, the principles of reducing profile and reinforcing the stent are still apparent because a greater volume of a therapeutic agent can be delivered by a coated sintered stent than a coated, solid stent having comparable dimensions.

The polymeric material that coats a sintered metal stent of the invention preferably comprises a biodegradable, bioabsorbable polymeric film that is capable of being loaded with and capable of releasing therapeutic drugs. The, polymeric coatings preferably include, but are not limited to, polycaprolactone (PCL), poly(DL-lactic acid) (DL-PLA) and poly(L-lactic acid) (L-PLA) or lactide. Other biodegradable, bioabsorbable polymers such as polyorthoesters, polyiminocarbonates, aliphatic polycarbonates, and polyphosphazenes may also be suitable, and other non-degradable polymers capable of carrying and delivering therapeutic drugs may also be suitable. Examples of non-degradable synthetic polymers are polyurethane, polyethylene, polyethylene teraphthalate, ethylene vinyl acetate, silicone and polyethylene oxide (PEO). The polymeric layers, according to one embodiment, are to be loaded with a pharmacologic agent for use in localized drug therapy. As used in this description, the terms biodegradable, bioabsorbable, reabsorbable, degradable, and absorbable are meant to encompass materials that are broken down and gradually absorbed or eliminated by the body, whether these processes are due to hydrolysis, metabolic processes, or bulk or surface erosion. In each of the foregoing embodiments, one polymeric layer is preferably about 0.0001 to 0.002 inches thick.

The thin polymeric films used to coat the stent are preferably first intermixed with the drug or drugs to be delivered, and then are typically laminated or solvent cast to the surface of the metal structural member. Lamination processing methods and temperatures can vary widely depending on the polymers used and the temperature sensitivity of the loaded drugs. Alternatively, the metal structure of the stent can be encapsulated in the layers of polymeric material by solvent casting, melt processing, insert molding, and dip coating.

In one embodiment of the present invention, the coating 100 is bioabsorbable, but no therapeutic agent is loaded into the polymer. The coating 100 dissolves after implantation and this delays the time that the therapeutic agent is released into the vasculature of a patient. The thickness of the coating 100 as well as the rate at which the coating 100 is bioabsorbed determines the length of time that the stent is mounted into the vasculature before the therapeutic agent is delivered from the pores of the stent. Additionally, a therapeutic agent can be loaded into the bioabsorbable coating 100. Thus a therapeutic agent will be delivered by the stent at a rate determined by the bioabsorbability of the coating 100. Once the bioabsorbable material has completely dissolved, the therapeutic agent in the pores can be delivered at a rate determined by the pore size and porosity.

In another embodiment, it is preferred that the coating 100 is permeable and non-absorbable. In such circumstances, the rate at which the drugs permeate into the tissue is controlled by the physical properties of the particular coating 100 selected. Additionally, the coating 100 may be selected to reduce restenosis, thrombosis or other tissue inflammation. For example, a heparin coating is known in the art to reduce blood clotting. Heparin, when coated on a stent reduces clotting of blood on the surface of the stent. The heparin coating is affixed to the surface of the stent through ionic bonding, end point attaching, or photo-linking the heparin.

In yet another embodiment, a first therapeutic agent is loaded into the coating 100 and a second therapeutic agent is loaded into the pores of the stent. This may be the case when a series of drug dosages or concentrations are needed. When such a stent is placed into the vasculature, the first therapeutic agent is absorbed first by the vasculature and the second therapeutic agent is absorbed later by the vasculature. This variation adds a further dimension to drug treatment allowing for sequential drug therapy at the site of placement of the stent.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:
1. A stent comprising:
   a body substantially formed of a molybdenum-rhenium alloy including an interconnected network of struts,
   wherein the struts include a metallic core formed by large diameter particles defining a first porous region, and a second porous region and a third porous region formed by smaller diameter particles, such that the first porous region is disposed between the second porous region and third porous region and the average pore size of the first porous region is greater than the average pore size of the second porous region and the average pore size of the third porous region.

2. The stent of claim 1, wherein the struts are self-expandable or balloon expandable.

3. A stent comprising a strut element, the strut element being at least partially formed of a molybdenum-rhenium alloy,
   wherein the strut element includes a solid metallic inner core having an inner side and an opposed, outer side,
   an outer layer disposed on the outer side, the outer layer being a first porous layer of metallic material formed by particles, filaments or fibers sintered to the inner core, and
   an inner layer disposed on the inner side, the inner layer being a second porous layer of metallic material formed by particles, filaments or fibers sintered to the inner core,
   wherein the strut is formed from a metallic sheet such that the solid core causes a therapeutic agent loaded into the second porous layer to flow only in a radially inward direction after the stent has been implanted in a vessel, and
   wherein the stent is configured for being radially expanded by a balloon and for providing support to a body vessel after the stent has been radially expanded by the balloon.

4. The stent of claim 3, wherein the outer layer is capable of contacting the inner wall of the vessel when the stent has been implanted in the vessel.

5. The stent of claim 3, wherein the outer layer is formed by sintering metallic particles.

6. The stent of claim 3, wherein the outer layer has a porosity greater than 0.30.

7. The stent of claim 3, wherein the outer layer is formed by sintering a matrix of overlapping metallic filaments.

8. A stent comprising:
   a body at least partially formed of a molybdenum-rhenium alloy including an interconnected network of struts,
   wherein the struts include a first porous metallic layer, a second porous metallic layer, and a metallic core, and
   the first and second layers are located on opposite sides of the metallic core,
   the first porous layer is formed from particles having a first diameter, thereby forming a first average pore size,
   the second porous layer is formed from particles having a second diameter, thereby forming a second average pore size, and
   the first average pore size is greater than the second average pore size.

9. The stent of claim 8, wherein a therapeutic agent is disposed within the first or second porous outer layer.

10. The stent of claim 8, wherein the stent is self-expandable or balloon expandable.

11. A stent comprising:
   a body substantially formed of a molybdenum-rhenium alloy including an interconnected network of struts,
   wherein the struts include a second porous region, a third porous region, and a first porous region disposed between the second porous region and third porous region,
   wherein the average pore size of the first porous region is greater than the average pore size of the second porous region and the average pore size of the third porous region, and
   wherein the stent has a therapeutic agent loaded into the first porous region, and
   wherein the first porous region is devoid of a polymer layer for purposes of delivering therapeutic agents.

* * * * *